(12) United States Patent
Dadd et al.

(10) Patent No.: US 8,805,546 B2
(45) Date of Patent: Aug. 12, 2014

(54) COCHLEAR ELECTRODE WITH PRECURVED AND STRAIGHT SECTIONS

(75) Inventors: Fysh Dadd, Lane Cove (AU); Robert Briggs, East Melbourne (AU); Robert Cowan, Prahran (AU); Peter Gibson, South Coogee (AU); Sharam Manouchehri, Auburn (AU); Claudia Tasche, Elanora Heights (AU)

(73) Assignee: Hearworks Pty, Ltd, East Melbourne, Victoria (AU)

( * ) Notice: Subject to any disclaimer, the term of this patent is extended or adjusted under 35 U.S.C. 154(b) by 247 days.

(21) Appl. No.: 11/219,824

(22) Filed: Sep. 7, 2005

(65) Prior Publication Data

US 2006/0085055 A1  Apr. 20, 2006

(30) Foreign Application Priority Data

Sep. 9, 2004 (AU) ................. 2004905111

(51) Int. Cl.
*A61N 1/05* (2006.01)
(52) U.S. Cl.
USPC ........................................... 607/137; 607/57
(58) Field of Classification Search
USPC ............................................... 607/55–57, 137
See application file for complete search history.

(56) References Cited

U.S. PATENT DOCUMENTS

| | | | |
|---|---|---|---|
| 4,357,497 A | 11/1982 | Hochmair et al. | |
| 4,532,930 A | 8/1985 | Crosby et al. | |
| 4,686,765 A | 8/1987 | Byers et al. | |
| 4,819,647 A | 4/1989 | Byers et al. | |
| 5,037,497 A | 8/1991 | Stypulkowski | |
| 5,545,219 A * | 8/1996 | Kuzma | 623/10 |
| 5,578,084 A | 11/1996 | Kuzma et al. | |
| 5,645,585 A * | 7/1997 | Kuzma | 623/10 |
| 5,653,742 A | 8/1997 | Parker et al. | |
| 5,720,009 A | 2/1998 | Kirk et al. | |
| 5,999,859 A | 12/1999 | Jolly | |
| 6,038,484 A * | 3/2000 | Kuzma | 607/137 |
| 6,070,105 A | 5/2000 | Kuzma | |
| 6,078,841 A * | 6/2000 | Kuzma | 607/137 |

(Continued)

FOREIGN PATENT DOCUMENTS

| | | |
|---|---|---|
| JP | 05-049701 | 3/1993 |
| JP | 10-234866 | 9/1998 |

(Continued)

OTHER PUBLICATIONS

Corresponding Australian Search Report from Application No. PR1780, dated Jan. 18, 2001, 3 pages.

(Continued)

*Primary Examiner* — Eric D. Bertram
(74) *Attorney, Agent, or Firm* — K&L Gates, LLP

(57) ABSTRACT

An implantable electrode array for insertion into an implantee's body. The array comprises an elongate carrier having a proximal end and a distal end. A plurality of electrodes are supported by the carrier at respective longitudinally spaced locations thereon between the proximal end and the distal end. The carrier is comprised of at least a first portion that preferentially adopts a first at least partially curved configuration and at least a second portion that preferentially adopts a second different configuration to that of the first portion. The second portion is closer to the distal end than the first portion and both the first and second portions each have at least one electrode supported thereon.

30 Claims, 11 Drawing Sheets

(56) References Cited

U.S. PATENT DOCUMENTS

| | | | |
|---|---|---|---|
| 6,112,124 A * | 8/2000 | Loeb | 607/137 |
| 6,119,044 A | 9/2000 | Kuzma | |
| 6,125,302 A | 9/2000 | Kuzma | |
| 6,144,883 A | 11/2000 | Kuzma | |
| 6,195,586 B1 | 2/2001 | Kuzma | |
| 6,374,143 B1 | 4/2002 | Berrang et al. | |
| 6,397,110 B1 | 5/2002 | Kuzma | |
| 6,421,569 B1 | 7/2002 | Treaba et al. | |
| 6,604,283 B1 * | 8/2003 | Kuzma | 29/857 |
| 6,757,970 B1 | 7/2004 | Kuzma et al. | |
| 7,367,992 B2 | 5/2008 | Dadd | |
| 7,406,352 B2 | 7/2008 | Gibson | |
| 7,451,000 B2 | 11/2008 | Gibson et al. | |
| 2003/0036790 A1 | 2/2003 | Corbett et al. | |
| 2003/0236562 A1 | 12/2003 | Kuzma | |
| 2004/0030376 A1 * | 2/2004 | Gibson et al. | 607/137 |
| 2004/0116995 A1 | 6/2004 | Dadd | |
| 2004/0127968 A1 | 7/2004 | Kuzma et al. | |
| 2004/0172118 A1 | 9/2004 | Gibson | |
| 2004/0220651 A1 * | 11/2004 | Kuzma et al. | 607/137 |
| 2004/0243212 A1 | 12/2004 | Dadd et al. | |

FOREIGN PATENT DOCUMENTS

| | | | | |
|---|---|---|---|---|
| JP | 11-502441 | | 3/1999 | |
| WO | WO-9306698 | | 4/1993 | |
| WO | WO-9710784 | | 3/1997 | |
| WO | WO 03/070133 | | 8/2003 | |
| WO | WO 2004/050056 | * | 6/2004 | A61K 9/00 |
| WO | WO 2004/026199 | | 8/2004 | |

OTHER PUBLICATIONS

Examiner's First Report on Australian Application No. 2005205816, Issued Jul. 23, 2010, 3 pages.
Office Action Issued Oct. 19, 2010 in Canadian Application No. 2,409,815, 2 pages.
Office Action Issued Oct. 30, 2007 in European Application No. 01998139, 7 pages.
Supplementary Partial European Search Report issued Apr. 27, 2007 in European Application No. 01998139, 4 pages.
Office Action Issued Nov. 20, 2008 in European Application No. 01998139, 3 pages.
Supplementary European Search Report issued Jul. 17, 2007 in European Application No. 10998139, 5 pages.
International Preliminary Examination Report of PCT/AU2001/001541 dated Sep. 20, 2002, 11 pages.
International Search Report of PCT/AU2001/001541 dated Dec. 11, 2001, 2 pages.
International Search Report for Australian Application PR 3646 dated May 23, 2001, 2 pages.
Notice of Allowance issued Jul. 9, 2008 in U.S. Appl. No. 10/332,515, 4 pages.
Office Action Issued Feb. 13, 2006 in U.S. Appl. No. 10/332,515, 19 pages.
Office Action issued May 3, 2007 in U.S. Appl. No. 10/332,515, 10 pages.
Office Action Issued Oct. 12, 2007 in U.S. Appl. No. 10/332,515, 15 pages.
Office Action Issued Oct. 27, 2006 in U.S. Appl. No. 10/332,515, 18 pages.

* cited by examiner

COCHLEAR ELECTRODE WITH PRECURVED AND STRAIGHT SECTIONS

CROSS-REFERENCE TO RELATED APPLICATIONS

This application claims the priority of Australian Patent No. 2004905111, entitled, "Cochlear Electrode with Precurved and Straight Sections," filed on Sep. 9, 2004. The entire disclosure and contents of the above application are hereby incorporated by reference herein.

BACKGROUND

1. Field of the Invention

The present application relates generally to an implantable device and, more particularly, to an implantable cochlear electrode assembly.

2. Related Art

In many people who are profoundly deaf, the reason for their deafness is sensorineural hearing loss. This type of hearing loss is due to the at least partial absence of, or destruction of, the hair cells in the cochlea which transduce acoustic signals into nerve impulses. Cochlear™ implants bypass the hair cells and deliver electrical stimulations to the auditory nerve fibres thereby allowing the brain to perceive a hearing sensation resembling the natural hearing sensation normally delivered to the auditory nerve.

The implantable component of the cochlear implant typically comprises a receiver antenna coil and a stimulator unit that processes coded signals delivered from an external component and outputs a stimulation signal to an intracochlear electrode assembly which applies the electrical stimulation to the auditory nerve.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to one aspect, the present invention is an implantable electrode array for insertion into an implantee's body, the array comprising: an elongate carrier having a proximal end and a distal end; and a plurality of electrodes supported by the carrier at respective longitudinally spaced locations thereon between the proximal end and the distal end; wherein the carrier is comprised of a first portion that preferentially adopts a first at least patially curved configuration and at least a second portion that preferentially adopts a second different configuration to that of the first portion, said second portion being closer to said distal end than said first portion; and further wherein both the first and second portions each have at least one electrode supported thereon.

BRIEF DESCRIPTION OF THE DRAWINGS

By way of example only, the invention is described with reference to the accompanying drawings, in which.

DETAILED DESCRIPTION

While the depicted embodiment is directed to an implantable electrode array for implantation in the cochlea, it will be appreciated that the present invention has broader application and could be implantable in other suitable locations within an implantee.

Figure 1A:
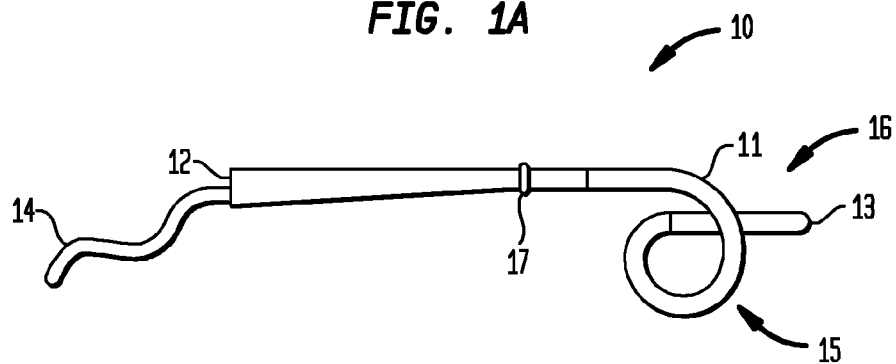
FIGS. 1A-1C are pictorial representations of one embodiment of a cochlear implant electrode array of the present invention.
Figure 1B:
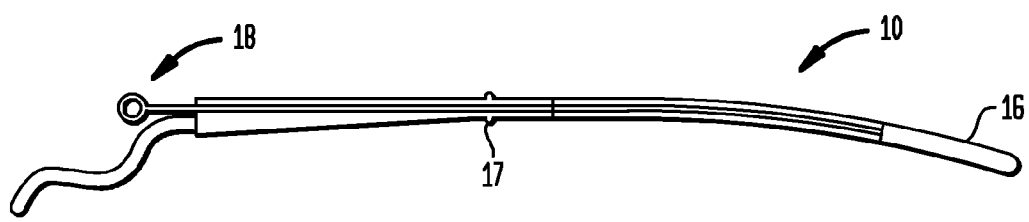
Figure 1C:
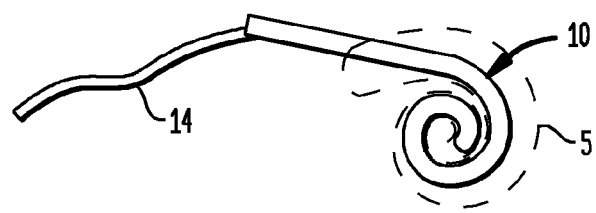

One embodiment of an implantable electrode array for insertion into the cochlea of an implantee is depicted generally as 10 in FIGS. 1A-1C. The array 10 comprises an elongate carrier 11 having a proximal end 12 and a distal tip or end 13. It will be understood that the carrier 11 supports a plurality of electrodes at respective longitudinally spaced locations thereon between the proximal end 12 and the distal end 13. The electrodes are not visible in FIGS. 1A-1C for reasons of drawing clarity. Electrical signals are delivered from an implanted stimulator unit (not visible) through a cable or lead 14 to the electrodes. It will be understood that the electrodes can be equally spaced along the carrier 11, non-equally spaced or be equally spaced for a length of the carrier 11 and also non-equally spaced for a length of the carrier 11.

The depicted carrier 11 is comprised of a first portion 15, which in turn has at least a portion thereof that preferentially adopts a first at least partially curved configuration. Said portion of the first portion 15 or the entire first portion 15 can be partially, substantially or fully straightened but is formed such that it prefers to adopt a curved configuration, with one example of a curved configuration depicted in FIG. 1A. The carrier 11 also comprises a second portion 16 that preferentially adopts a second different configuration to that of the first portion. In this embodiment, this second different configuration is a substantially straight configuration. It will be appreciated that the second different configuration could have a degree of curvature that would typically be less than the degree of curvature of the first portion 15 or be straight. While depicted as substantially straight, the second portion 16 is sufficiently flexible such that it is able to conform to the shape of the implant location (eg cochlea 5) following its implantation therein (see FIG. 1C).

As depicted, the second portion 16 is closer to the distal end 13 than the first portion 15. In the depicted embodiment, the carrier 11 is comprised of the first portion 15 and the second portion 16 between its proximal end 12 and distal end 13. As depicted, in the embodiment shown in FIG. 1A, the first portion 15 itself is comprised of a portion that is substantially straight for a length away from the cochleostomy marker 17 and then a curved portion. It will be appreciated that in other embodiments, the carrier 11 could be comprised of additional portions than that depicted. Still further, the entire length of the first portion 15 could have a degree of curvature.

In looking at the depicted carrier 11, it is to be understood that both the first portion 15 and the second portion 16 each have at least one electrode supported thereon. The second portion 16 could support one or more electrodes.

The carrier 11 has an extracochlear part and an intracochlear part. The extracochlear part extends from the proximal end 12 to the cochleostomy marker 17. The portion that is adapted to enter the cochlea, i.e., the intracochlear part, extends from the marker 17 to the distal end 13.

Figure 3A:
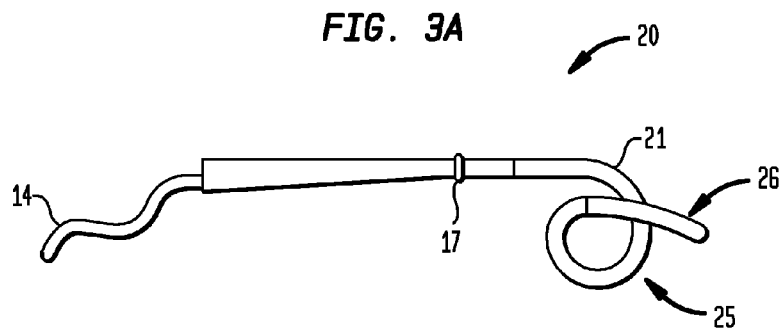
FIGS. 3A-3C are pictorial representations of another cochlear implant electrode array in accordance with embodiment of the present invention.

While FIGS. 1A-1C depict a straight substantially second portion 16, FIG. 3A depicts an alternative array 20 having a carrier 21 in which the second portion 26 is non-straight and has instead a degree of curvature. In the depicted embodiment, the second portion 26 preferentially adopts a curved configuration having a degree of curvature less than the curved portion of the first portion 25.

Figure 2A:
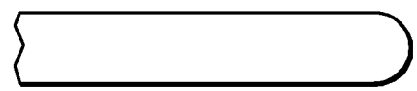
FIGS. 2a-2c are diagrammatic, not to scale, representations of the electrode carrier in accordance with one embodiment of the present invention.
Figure 2B:
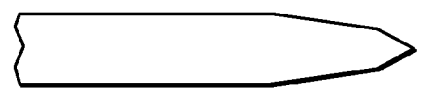
Figure 2C:

As depicted in FIG. 2, the carrier 11 can have a constant diameter for some or all of its length (FIG. 2a), can taper in diameter for at least a portion of its length between the proximal end 12 and the distal end 13 (FIG. 2b), and even be comprised of a mixture of constant diameter and tapering diameter portions (FIG. 2c).

In the depicted embodiments, the intracochlear part of the carrier 11 can have a length between about 8 mm and about 40 mm. The first portion can have a length between about 8 mm and about 34 mm, for example about 18 mm while the second portion can have a length between about 1 mm and 10 mm, more preferably about 3 mm.

The carrier 11 can be formed in various cross-sectional shapes and even comprise a number of different cross-sectional shapes. For example, the shape(s) may be circular, oval, hexagonal, octagonal, or a mixture of these and/or others.

The distal end 13 is preferably at least substantially hemispherical in form so that it presents a relatively soft and blunt shape to the inside of the cochlea during implantation.

In the depicted embodiments, the carriers 10,20, following implantation, are preferably positioned such that first portion 15,25 subtends an angle up to 650°, and more preferably about 360° within the basal section of the cochlea 5. The second portion 16,26 subtends an angle up to 360°, and more preferably about 270° within the apical section of the cochlea 5.

The carrier of the implantable electrode array can be formed of a relatively soft and resiliently flexible biocompatible material. The material can be an elastomeric material and/or a polymeric material. In one embodiment, the carrier 11,21 can be formed from a liquid silicone rubber, such as LSR30, LSR60 and the like, or an elastomer, such as HCRP 50, or a combination thereof.

In one embodiment, the first portion 15 can be formed from a different material to that of the second portion 16. For example, the first portion 15 can be formed of a relatively hard durometer silicone so as to ensure it recoils to its desired shape whereas the second portion 16 is formed of a relatively soft and resiliently flexible durometer material since it should not have to recoil, in use.

Figure 3B:
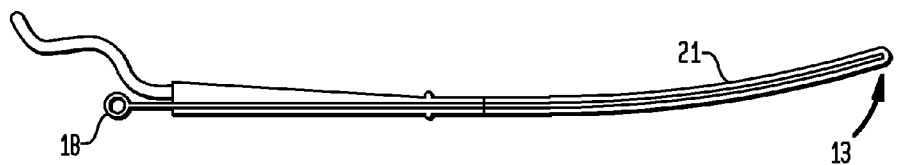

As depicted in FIGS. 1B and 3B, the carriers can be at least substantially straightened by a removable straightening element extending through the carrier. In one embodiment, the element can be formed of a biocompatible material. In the depicted embodiment, the element comprises a platinum stylet 18. An embodiment that does not rely on a stylet is described below. In other embodiments, the element could be formed of other suitable materials, including titanium, a plastics material, or a combination of metals, alloys and plastics materials.

The stylet can be circular in cross-section or can be molded or stamped in a variety of profiles to create the desired properties required of the stylet. A platinum stylet can be left hardened as drawn or at least a portion thereof can be annealed. For example, a distal portion at and/or adjacent the distal end can be annealed.

Figure 3C:
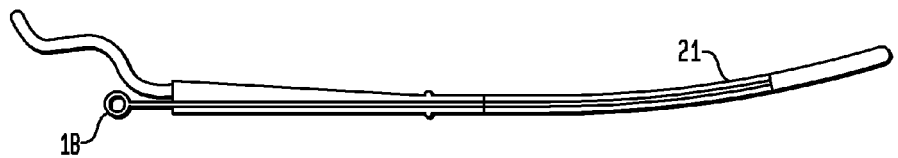

As depicted by FIG. 3B, the stylet 18 can extend to the distal end 13 of the carrier 21 or, as depicted in FIG. 3C, can instead only extend to the end of the first portion 25. It will be appreciated that the distal end of the stylet 18 could extend to a still different location including between the two depicted locations.

The stylet 18 is not necessarily needed to straighten the second portion 26 but can be used to create the desired mechanical properties required of the second portion 26 during the implantation procedure. For example, it would be expected that the second portion 26 will be more flexible with the stylet 18 not present than the case when it is. In an arrangement where the stylet does not extend into the second portion 26, the second portion can be formed of a relatively harder durometer silicone than the first portion 25 than maybe needs to be case in the arrangement where the stylet 18 does extend to the distal end of the carrier 21.

In one embodiment, the stylet 18 is positioned within a lumen extending through the carrier 20. The stylet can come in different lengths or the lumen does or does not extend into the second portion 26 depending on the arrangement being sought.

The depicted electrode arrays can be inserted into the cochlea using a variety of insertion methods and tools. For example, the carrier 11 can be inserted fully or partially into the cochlea prior to withdrawal of the stylet 18. Alternatively, an Advance Off-Stylet (AOS) mode can be employed in which the insertion of the carrier and withdrawal of the stylet happens simultaneously.

Figure 4A:
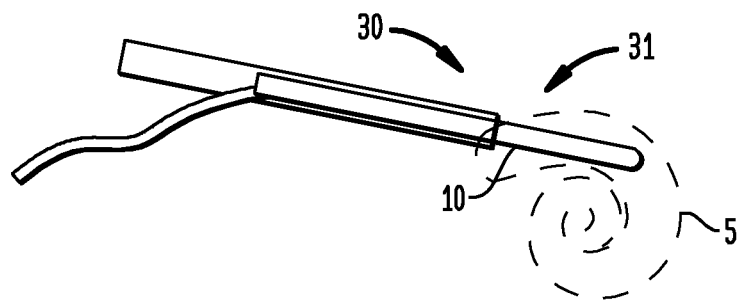
FIGS. 4A-4c depict diagrammatically insertion of the array into a cochlea using an insertion tool in accordance with embodiment of the present invention.
Figure 4B:
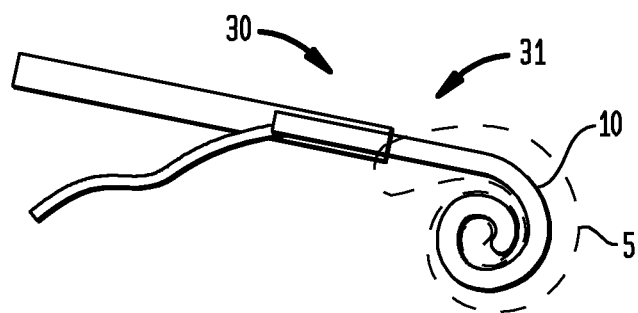
Figure 4C:
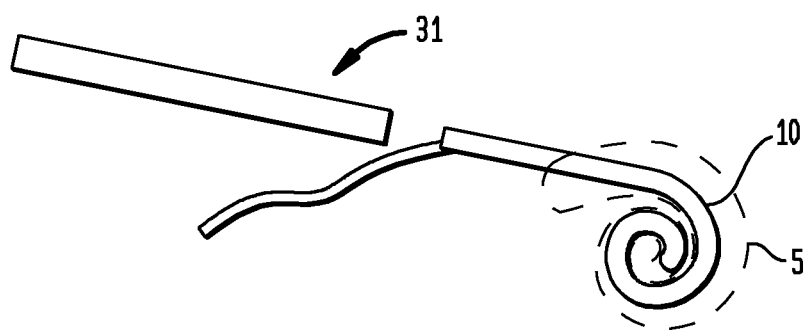

It will also be appreciated that the carrier could be implanted using a variety of insertion tools that are used with or without a stylet. In one embodiment, as depicted in FIGS. 4A-4C, insertion can be undertaken using an insertion tool having a tubular tip cartridge 30. In one embodiment, the tool having a tubular tip cartridge can be used in conjunction with a carrier having a stylet, such as that depicted in FIGS. 1B and 3B. In another embodiment, the tool could be used in conjunction with a carrier that does not have a stylet or lumen.

In the arrangement depicted in FIGS. 4A-4C, the cartridge 30 of an insertion tool serves to hold the first portion 15 straight during implantation. The tip 31 of the insertion tool 30 is rested on the cochleostomy during the procedure and allows the carrier to be slid through the cochleostomy and into the cochlea 5.

It is anticipated that various manufacturing methods can be utilized to manufacture the electrode arrays described herein.

Figure 5A:
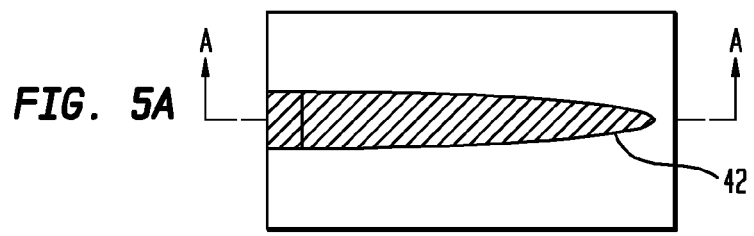
FIGS. 5A-5N depict some of the steps for manufacturing an electrode array in accordance with embodiment of the present invention.
Figure 5B:
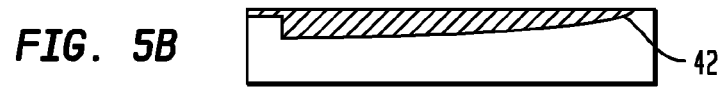
Figure 5C:
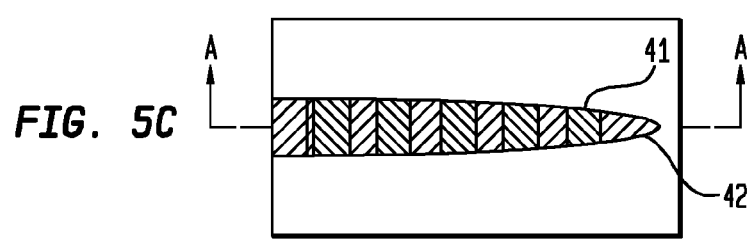
Figure 5D:
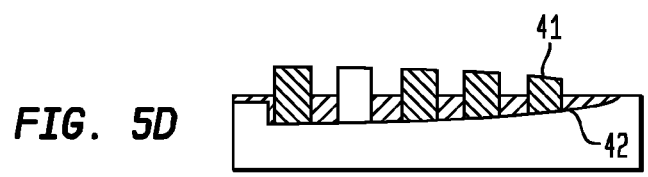
Figure 5E:
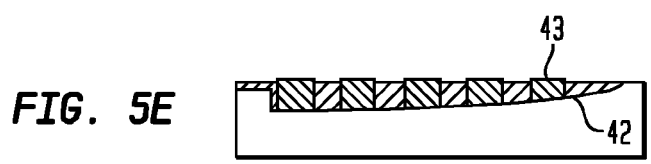
Figure 5F:
Figure 5G:
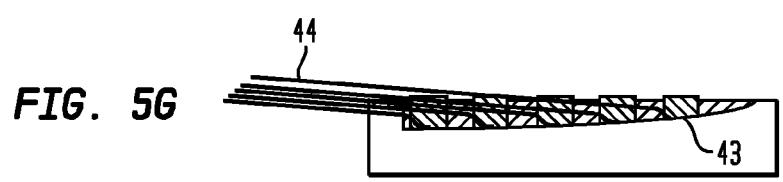
Figure 5H:
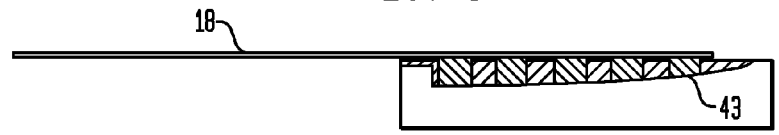
Figure 5I:
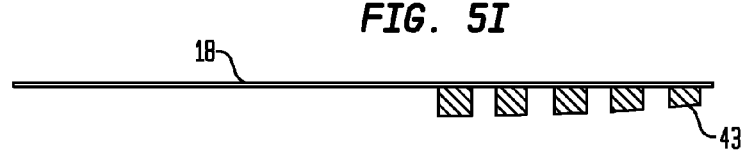
Figure 5J:
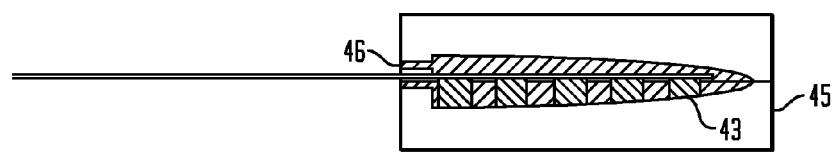
Figure 5K:
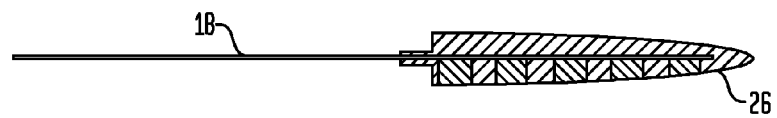
Figure 5L:
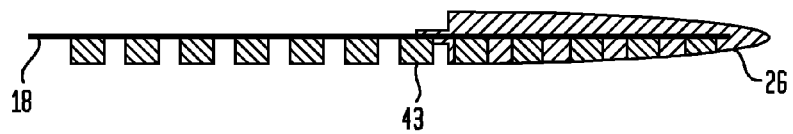
Figure 5M:
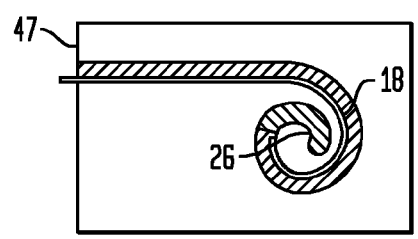
Figure 5N:
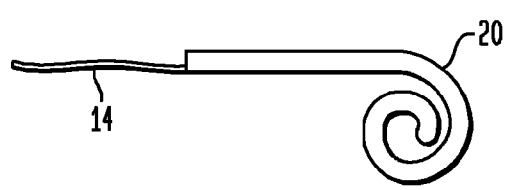

One embodiment of a manufacturing method for forming an electrode array is described herein with reference to FIGS. 5A-5N. In this embodiment, the stylet 18 is used in the array and is positioned so as to extend to the distal end of the carrier, such as is depicted in FIG. 3B. It will be appreciated that the array could be formed without a stylet in place.

In this embodiment, the second portion 26 is molded first and once formed is then placed in a curved mold to allow completion of the molding of the first precurved portion 25.

One initial step is the formation of the rings 41 (in this embodiment, formed of platinum) that will constitute the electrodes of the array. In one embodiment, the platinum rings 41 can be formed to a desired width by being cut from a platinum tube.

The rings 41 are then placed in a jig for forming and welding. To achieve this, the rings 41 can be placed in a cavity 42 as depicted in FIGS. 5C and 5D. Once positioned, the rings 41 can be squashed to form half rings 43 (see FIGS. 5E and 5F). Electrically conducting wires 44 can then be spot welded to each of the half rings 43 to form the array (FIG. 5G).

A further step comprises preparing a stylet 18 for the array. As depicted in FIG. 5H, the stylet 18 can be positioned relative to the half rings 43 and held in place with a few drops of a suitable silicone prior to the welded assembly being removed from the jig (See FIG. 5I). It is to be appreciated that in considering FIGS. 5H and 5I, the wires 44 are not shown for reasons of clarity.

FIGS. 5J and 5K depict steps of overmolding the welded assembly with silicone to form the second portion 26. This comprises placing the welded assembly in the bottom half 45 of a two part mold and then injecting liquid silicone rubber (LSR) into the mold through port 46. The precise type of LSR may be selected for hardness, elasticity and other properties to suit the required stiffness and flexibility of the array.

The steps depicted by FIGS. 5A-5E can be repeated to form the welded assembly of the first portion 25. Once prepared, the welded assembly can be attached to the free end of the production stylet 18 by a few drops of silicone (see FIG. 5L). Note that for clarity, not all the rings that would be present in the first portion 25 are shown in FIG. 5L.

A further step comprises overmolding the first portion 25 and the second portion 26 with an overmold. To achieve this, the welded assembly is placed in the bottom half of an overmold 47 as shown in FIG. 5M. The mold can then be filled with an elastomer (e.g. HCRP50) or alternatively LSR can be injected into the mold after the top half of the mold is put in place. When using elastomer, the top half of the mold is clamped in place and an appropriate temperature and pressure is applied as required to cure the chosen elastomer.

Once cured, the overmolded electrode array can be lifted out of the overmold and the production stylet 18 can then be carefully withdrawn so leaving a lumen up to the distal end of the first portion 25. The result is the array depicted in FIG. 5N.

In an alternative method where the stylet only extends to the distal end of the first portion 25, the process is identical to that of the previous process, except that after fabricating the electrode described above the lumen of the second portion 26 is backfilled by injecting it with LSR from the tip.

Figure 6A:
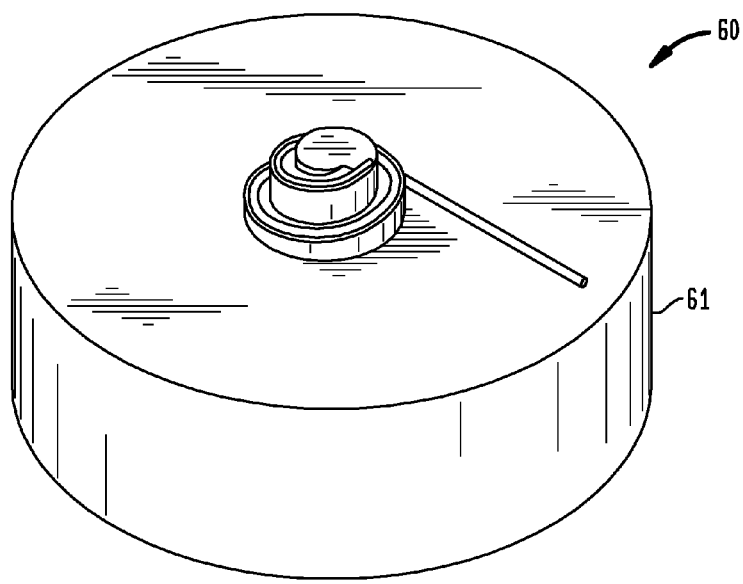
FIGS. 6a-6e depict some of the steps in the use of a mold to form one embodiment of the array in accordance with embodiment of the present invention.
Figure 6B:
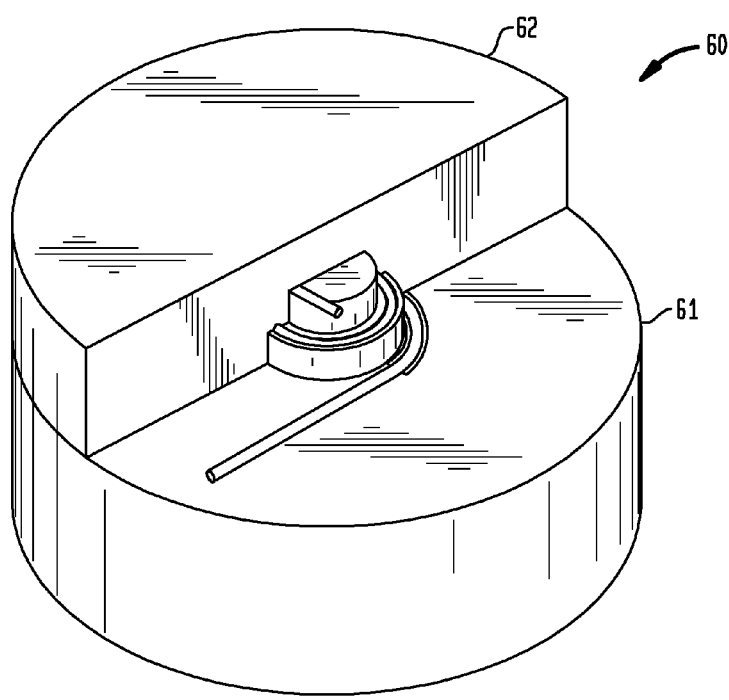
Figure 6C:
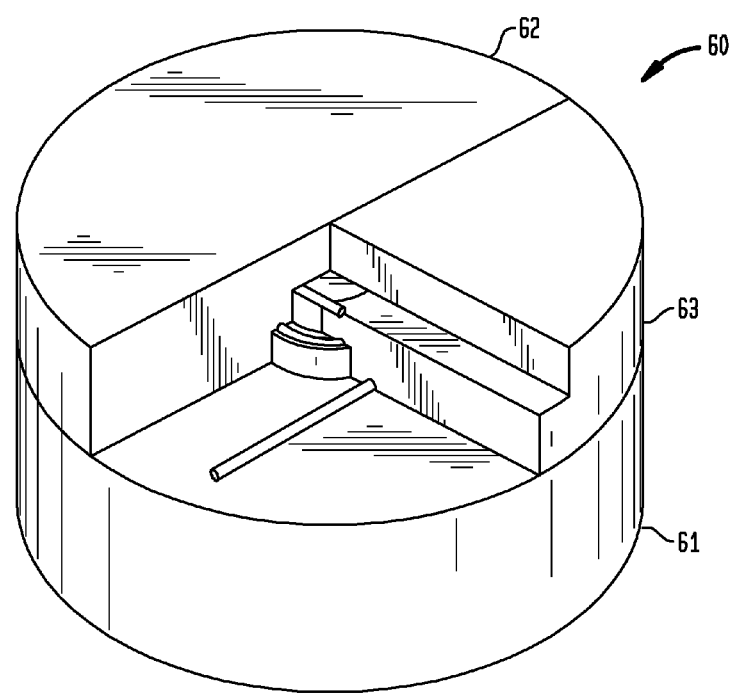
Figure 6D:
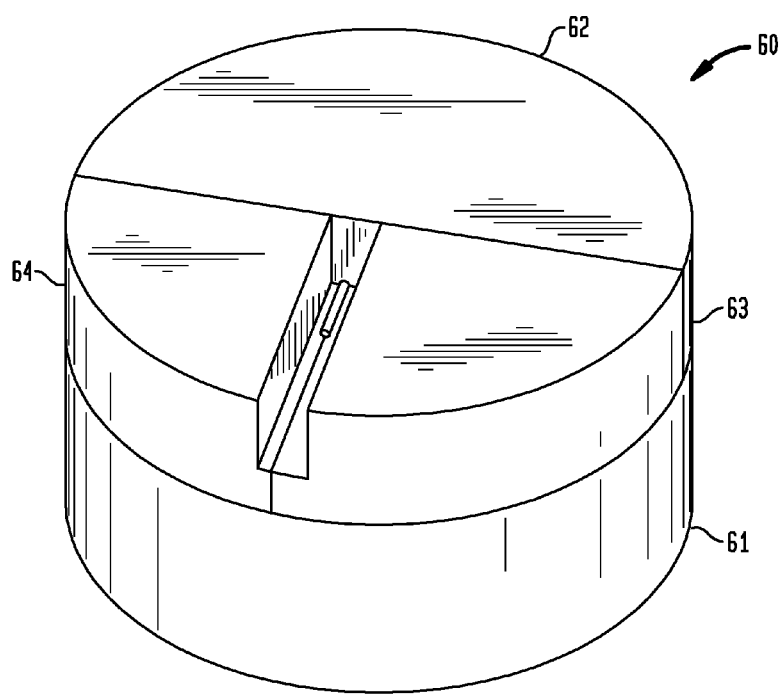
Figure 6E:
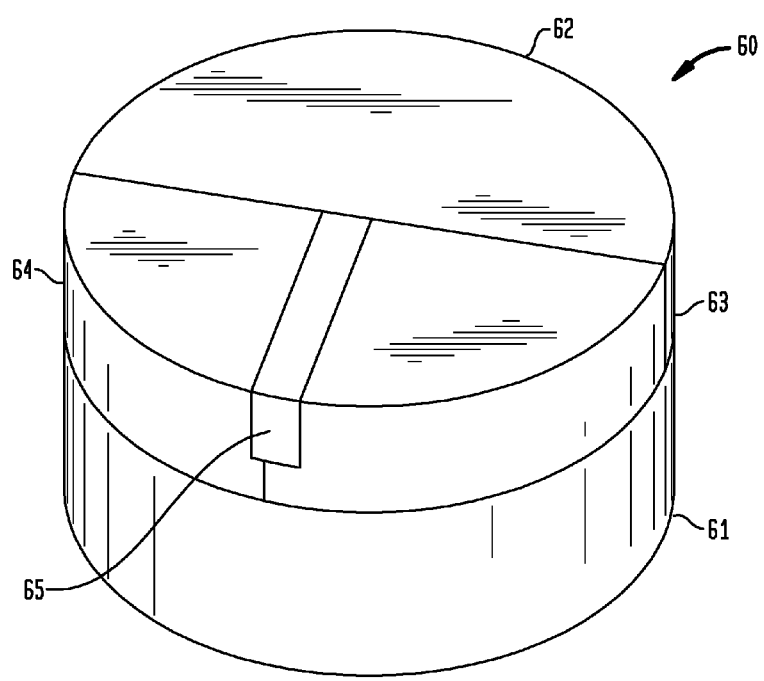

As depicted in FIGS. 6a-6e, the electrode array can also be molded in a mold 60 (which is fully depicted in FIG. 6e). The mold 60 is made up of a number of components (61, 62, 63, 64 and 65) that are put together to make up the mold 60. While the die of the mold extends in a third dimension (as depicted in FIG. 6a), the formed electrode array can be formed so as to adopt a planar configuration on removal from the mold 60. In an alternative embodiment, the parts of the array can be molded separately and then combined near the end of the manufacturing process to form the entire array.

The implantable electrode array as described herein is preferably adapted to cause relatively little, if any, trauma to the implant location (eg within the cochlea) during implantation. It is also preferably capable of being withdrawn from the cochlea, if this is ever desired, without causing significant trauma to the cochlea. At least some of the array is also designed to be positionable in an optimal position within the cochlea despite the variety of shapes and dimensions of the human cochlea that do exist in practice. For example, the configuration of the first portion is preferably such that the array adopts a desired position in the basal turn following implantation. The configuration of the second portion is preferably such that the size and shape of the cochlea serves to at least partially assist in ensuring appropriate placement of the array in the second and apical turns of the cochlea.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An implantable electrode array for insertion into an implantee's body, the array comprising:
    an elongate carrier having a first portion adjacent a proximal end and a second portion adjacent a distal end that does not overlap the first portion in the direction of longitudinal extension of the elongate carrier, the first portion being made of a first material and the second portion being made of a second material, the first portion comprising more of the first material than the second material, the second portion comprising more of the second material than the first material, the first and second materials having different mechanical properties, the first portion biased in a curved configuration and comprising a curve having an angle of curvature of about 360°, and the second portion biased in a substantially straight configuration; and
    a plurality of electrodes supported by the carrier at respective longitudinally spaced locations on the carrier, wherein each of the first portion and the second portion have at least one of the plurality of electrodes supported thereon.

2. The implantable electrode array of claim 1, wherein a portion of said first portion is configured to adopt a first at least partially curved configuration.

3. The implantable electrode array of claim 1, wherein the implantable electrode array is a cochlear implant electrode array insertable into the cochlear of an implantee.

4. The implantable electrode array of claim 3, wherein, following implantation, the second portion of the carrier subtends an angle of about 270° within the cochlea.

5. The implantable electrode array of claim 1, wherein the first portion has a length between about 8 mm and about 34 mm.

6. The implantable electrode array of claim 1, wherein the second portion has a length between about 1 mm and 10 mm.

7. The implantable electrode array of claim 6, wherein the second portion has a length of about 3 mm.

8. The implantable electrode array of claim 1, wherein the carrier is formed from an elastomeric and/or a polymeric material.

9. The implantable electrode array of claim 1, wherein the first portion is configured to adopt a first at least partially curved configuration and the second portion is configured to adopt a curved configuration having a degree of curvature less than that of the first portion.

10. The implantable electrode assembly of claim 9, wherein the second portion is conformable to the shape of a site of implantation.

11. The implantable electrode array of claim 9, wherein at least the first portion is at least substantially straightenable by a removable straightening element extending through the carrier.

12. The implantable electrode array of claim 11, wherein the straightening element is positioned within a lumen extending through the carrier.

13. The implantable electrode array of claim 11, wherein the straightening element extends to the distal end of the carrier.

14. The implantable electrode assembly of claim 9, wherein at least one of the plurality of electrodes is supported on the first portion and not supported on the second portion, and wherein at least one of the plurality of the electrodes is supported on the second portion and not supported on the first portion.

15. The implantable electrode array of claim 1, wherein the first and second materials have different hardness.

16. The implantable electrode array of claim 15, wherein the first and second materials are made of silicone, the first material being a harder durometer silicone than the second material.

17. The implantable electrode array of claim 16, wherein the second material is made of a soft and resiliently flexible durometer silicone.

18. The implantable electrode array of claim 1, wherein the distal end extends outside the curve of the first portion.

19. The implantable electrode array of claim 1, further comprising a lumen extending through the carrier.

20. The implantable electrode array of claim 19, wherein the lumen does not extend through the second portion.

21. The implantable electrode array of claim 20, wherein a stylet is insertable into the lumen to straighten the first portion.

22. An implantable electrode array for insertion into an implantee's body, the array comprising:
   an elongate carrier having a proximal end and a distal end and including:
      a first portion adjacent the proximal end and extending towards the distal end; and
      a second portion adjacent the distal end and extending towards the proximal end, wherein
      neither the first portion nor the second portion extend the entire length of the elongate carrier, the first portion has a distinct boundary defining limits of the first portion's extent in the distal direction of electrode array, the second portion has a distinct boundary defining limits of the second portion's extent in the proximal direction of the electrode array, the distinct boundaries are defined by the presence of a first material in the first portion and the presence of a second material in the second portion, the first and second materials have different mechanical properties, the first portion biased in a curved configuration and comprising a curve having an angle of curvature of about 360°, and the second portion biased in a substantially straight configuration; and
   a plurality of electrodes supported by the carrier at respective longitudinally spaced locations on the carrier, wherein each of the first portion and the second portion have at least one of the plurality of electrodes supported thereon.

23. The implantable electrode array of claim 22, wherein the first and second materials have different hardness.

24. The implantable electrode array of claim 23, wherein the first and second materials are made of silicone, the first material being a harder durometer silicone than the second material.

25. The implantable electrode array of claim 24, wherein the second material is made of a soft and resiliently flexible durometer silicone.

26. An implantable electrode array for insertion into an implantee's body, the array comprising:
   an elongate carrier having a first portion adjacent a proximal end and a second portion adjacent a distal end that does not overlap the first portion in the direction of longitudinal extension of the elongate carrier, the first portion being made of a first material and the second portion being made of a second material, the first portion comprising more of the first material than the second material, the second portion comprising more of the second material than the first material, the first and second materials having different mechanical properties, the first portion biased in a curved configuration and the second portion biased in a substantially straight configuration;
   a lumen extending through the carrier, wherein the lumen does not extend through the second portion; and
   a plurality of electrodes supported by the carrier at respective longitudinally spaced locations on the carrier, wherein each of the first portion and the second portion have at least one of the plurality of electrodes supported thereon.

27. The implantable electrode array of claim 26, wherein the curved configuration of the first portion comprises a curve having an angle of curvature of about 360°.

28. The implantable electrode array of claim 26, wherein the first and second materials have different hardness.

29. The implantable electrode array of claim 28, wherein the first and second materials are made of silicone, the first material being a harder durometer silicone than the second material.

30. The implantable electrode array of claim 29, wherein the second material is made of a soft and resiliently flexible durometer silicone.

* * * * *